United States Patent [19]

Shturman

[11] Patent Number: 5,356,418

[45] Date of Patent: Oct. 18, 1994

[54] APPARATUS AND METHOD FOR ROTATIONAL ATHERECTOMY

[75] Inventor: Leonid Shturman, Minneapolis, Minn.

[73] Assignee: Shturman Cardiology Systems, Inc., Minneapolis, Minn.

[21] Appl. No.: 967,765

[22] Filed: Oct. 28, 1992

[51] Int. Cl.$^5$ .............................................. A61B 17/32
[52] U.S. Cl. .................................. 606/159; 606/170; 606/180
[58] Field of Search ................ 606/159, 170, 171, 180; 604/22, 96

[56] References Cited

U.S. PATENT DOCUMENTS

| | | |
|---|---|---|
| Re. 33,569 | 4/1991 | Gifford, III et al. . |
| Re. 33,911 | 5/1992 | Samson et al. . |
| 4,445,509 | 5/1984 | Auth ................................ 606/159 |
| 4,534,363 | 8/1985 | Gold . |
| 4,679,557 | 7/1987 | Opie et al. . |
| 4,781,186 | 11/1988 | Simpson et al. . |
| 4,794,931 | 1/1989 | Yock . |
| 4,799,496 | 1/1989 | Hargreaves et al. . |
| 4,846,186 | 7/1989 | Box et al. . |
| 4,887,606 | 12/1989 | Yock et al. . |
| 4,917,097 | 4/1990 | Proudian et al. . |
| 4,917,103 | 4/1990 | Gambale et al. . |
| 4,926,858 | 5/1990 | Gifford, III et al. . |
| 4,979,951 | 12/1990 | Simpson . |
| 4,984,581 | 1/1991 | Stice . |
| 4,990,134 | 2/1991 | Auth ................................ 604/22 |
| 5,000,185 | 3/1991 | Yock . |
| 5,007,434 | 4/1991 | Doyle et al. . |
| 5,010,886 | 4/1991 | Passafaro et al. . |
| 5,024,234 | 6/1991 | Leary et al. . |
| 5,029,588 | 7/1991 | Yock et al. . |
| 5,042,985 | 8/1991 | Elliot et al. ...................... 604/96 |
| 5,047,040 | 9/1991 | Simpson et al. . |
| 5,053,044 | 10/1991 | Mueller et al. . |
| 5,054,492 | 10/1991 | Scribner et al. . |
| 5,067,489 | 11/1991 | Lind . |
| 5,069,217 | 12/1991 | Fleischhacker, Jr. . |

(List continued on next page.)

FOREIGN PATENT DOCUMENTS

| | | |
|---|---|---|
| 0359447 | 3/1990 | European Pat. Off. . |
| 0421457 | 4/1991 | European Pat. Off. ............ 606/159 |
| 9004657 | 8/1990 | PCT Int'l Appl. . |
| 9101813 | 3/1991 | PCT Int'l Appl. . |
| 9105844 | 8/1991 | PCT Int'l Appl. . |

OTHER PUBLICATIONS

"Rotablator ®, a Revolution in Angioplasty," Heat Technology Inc., Bellevue, Washington 98005 USA.

McCarty, Lyle H., "Catheter Clears Coronary Arteries", Design News, Sep. 23, 1991, pp. 88–92.

"Premier Presents Two Striper ® Dental Diamond Instruments," Abrasive Technology Inc., Westerville, Ohio USA.

Gilmore, H. W., et al, "Instrumentation," Operative (List continued on next page.)

Primary Examiner—Stephen C. Pellegrino
Assistant Examiner—William Lewis
Attorney, Agent, or Firm—Gregory P. Kaihoi

[57] ABSTRACT

Apparatus and method for performing an atherectomy. The apparatus includes a rotational atherectomy device having a flexible, elongated drive shaft and an abrasive burr carried on the drive shaft. The drive shaft and abrasive burr each include a central lumen so that they can be advanced over a guide wire. The apparatus further includes a guide wire having a generally straight proximal portion, a flexible distal end portion, and an intermediate, flexible burr positioning segment. The burr positioning segment includes a predetermined curved shape so that when the abrasive burr is advanced over the guide wire to a position along the curved burr positioning segment, the burr positioning segment positions the burr laterally away from the axes of the proximal and distal portions of the guide wire, thus giving control over the lateral position of the burr within an artery. The device therefore allows selective removal of tissue from one side of an artery, permitting selective treatment of eccentric lesions without damaging the artery wall, and permitting treatment of lesions generally without blocking blood flow during use.

14 Claims, 5 Drawing Sheets

U.S. PATENT DOCUMENTS

| | | |
|---|---|---|
| 5,071,424 | 12/1991 | Reger . |
| 5,074,871 | 12/1991 | Groshong . |
| 5,084,022 | 1/1992 | Claude . |
| 5,092,873 | 3/1992 | Simpson et al. . |
| 5,100,424 | 3/1992 | Jang et al. .................... 606/159 |
| 5,111,829 | 5/1992 | de Toledo . |
| 5,129,890 | 7/1992 | Bates et al. . |
| 5,135,516 | 8/1992 | Sahatjian et al. . |
| 5,135,535 | 8/1992 | Kramer . |

OTHER PUBLICATIONS

*Dentistry*, 4th Ed., Ch. 4, pp. 55, 64–73, The C. V. Mosby Company, 1982.

Gilmore, H. W., et al, *Operative Dentistry*, 4th Ed., pp. 348–351, 353–354, The C. V. Mosby Company, 1982.

"Premier Two Striper® Gingival Curettage," Abrasive Technology Inc., Westerville, Ohio USA.

"Premier Two Striper® Crown & Bridge Techniques," Abrasive Technology, Inc., Westerville, Ohio USA.

Tupac, Robert G., et al, "A Comparison of Cord Gingival Displacement with the Gingitage Technique," *The Journal of Prosthetic Dentistry*, Nov. 1981, vol. 46, No. 5, pp. 509–515.

*Atherectomy, A Physician's Guide*, Strategic Business Development, Inc., Kauai, Hawaii 96714 USA, 1990, pp. 1–114.

Bom, N., et al, "Early and Recent Intraluminal Ultrasound Devices," *International Journal of Cardiac Imaging*, 4:79–88, 1989.

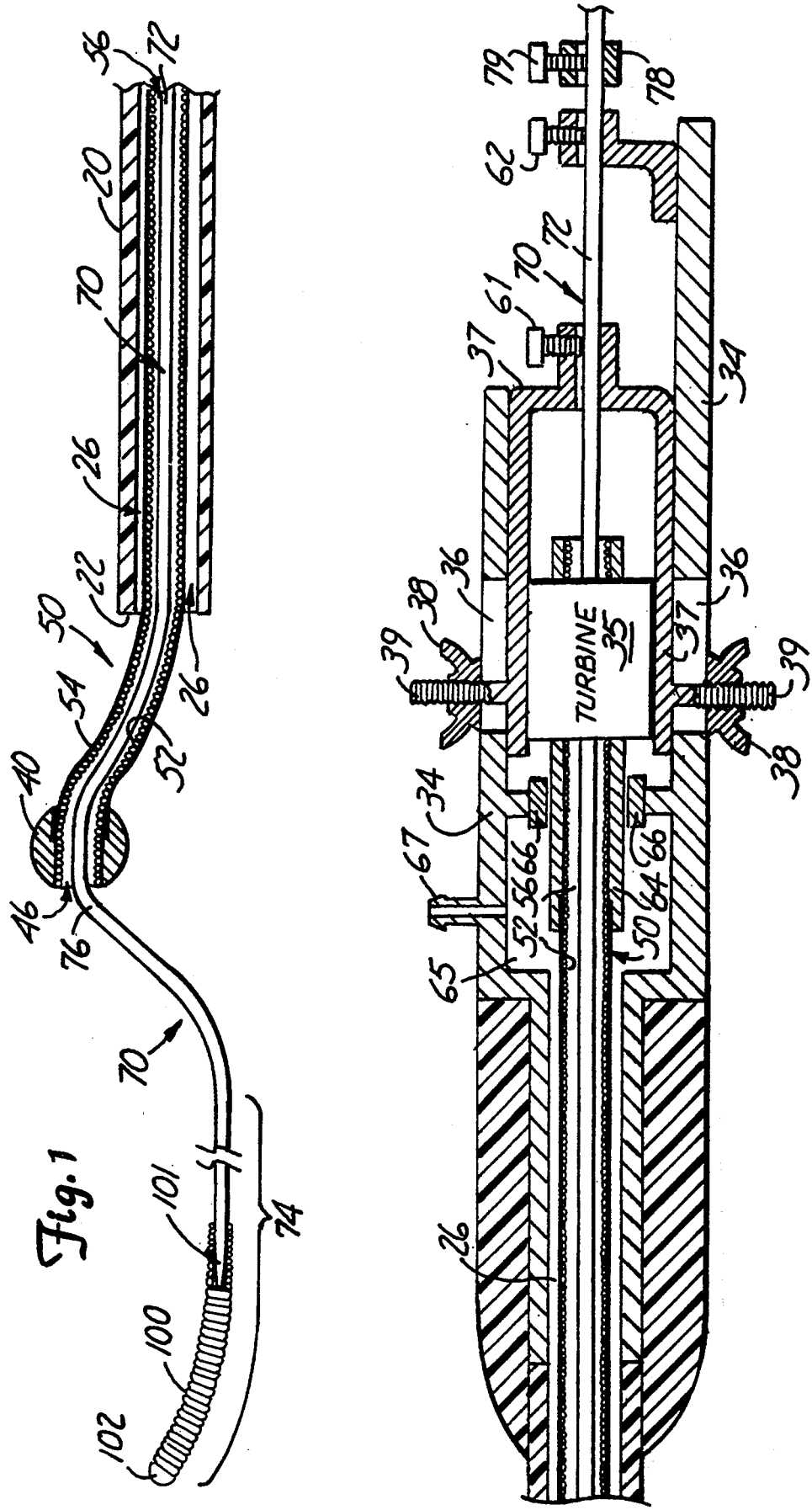

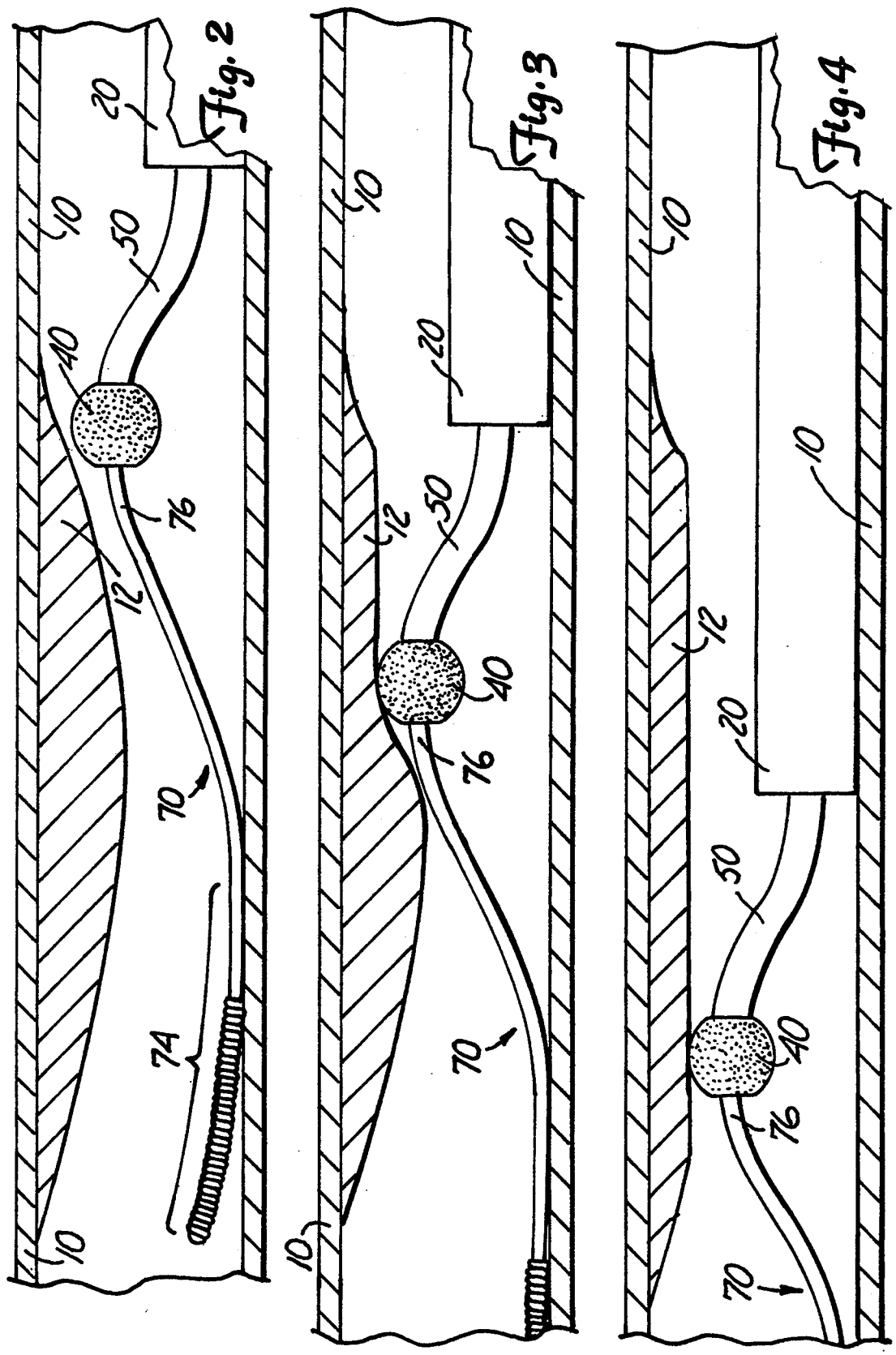

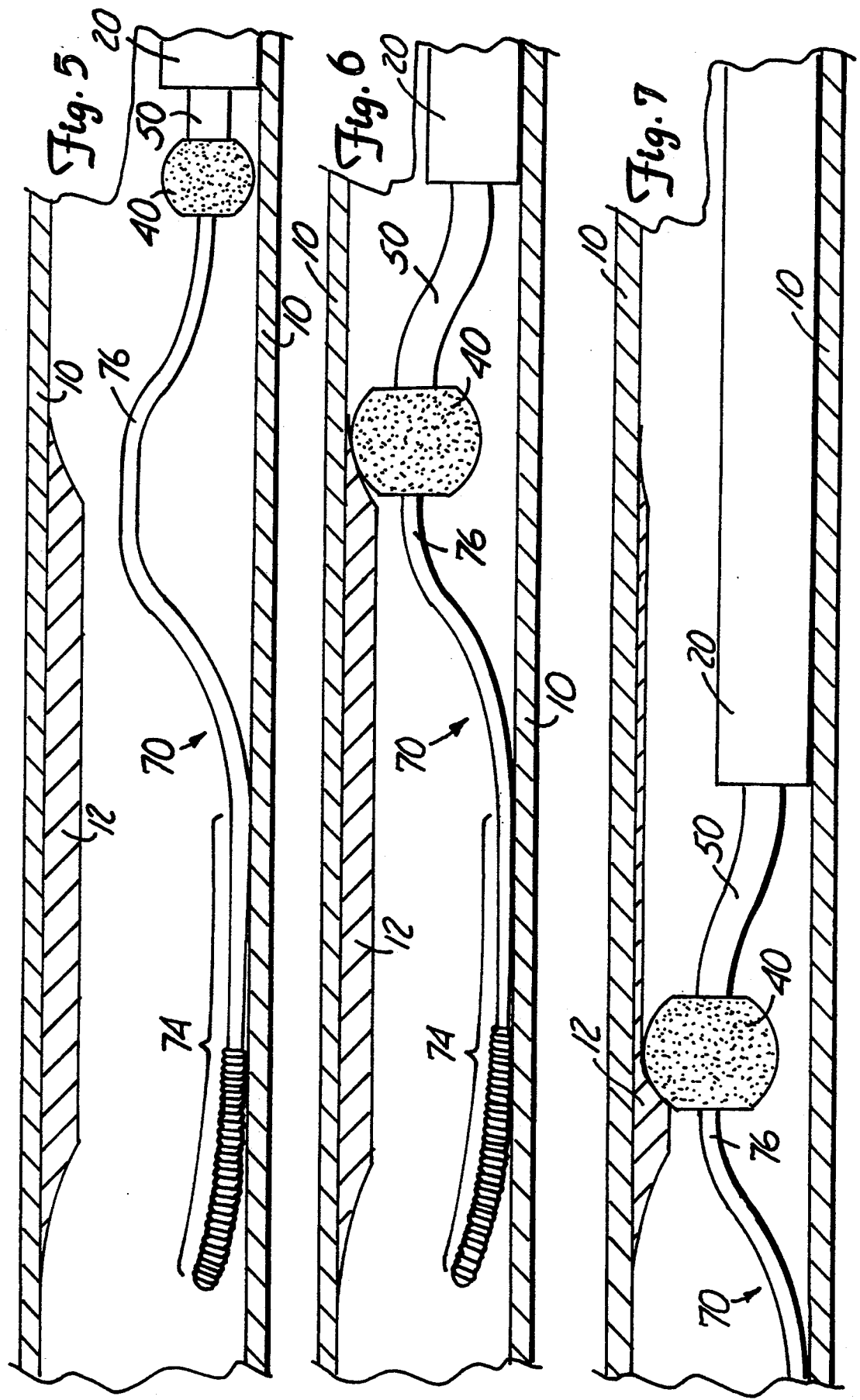

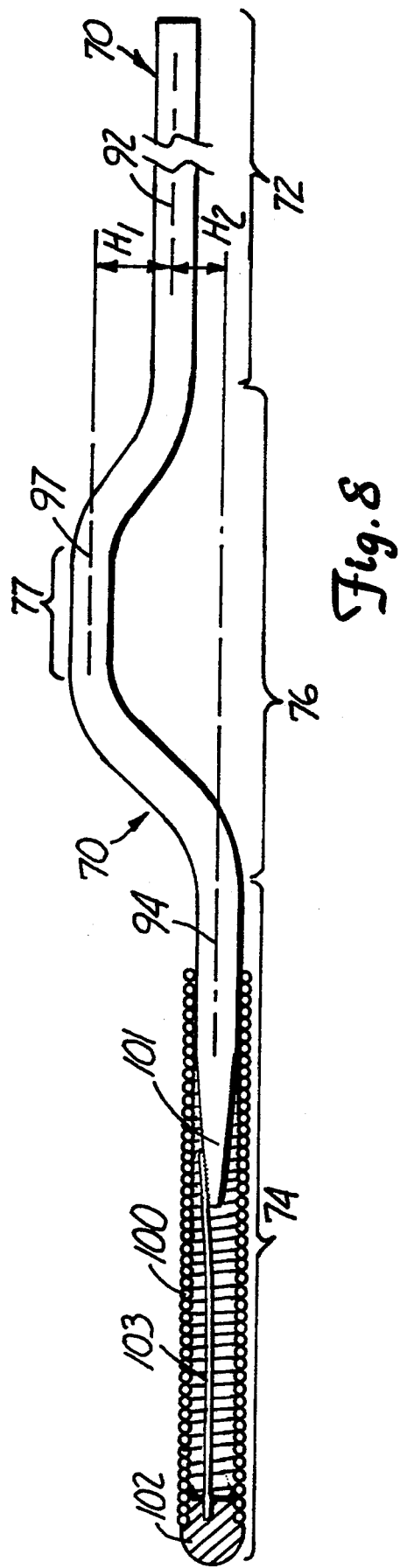
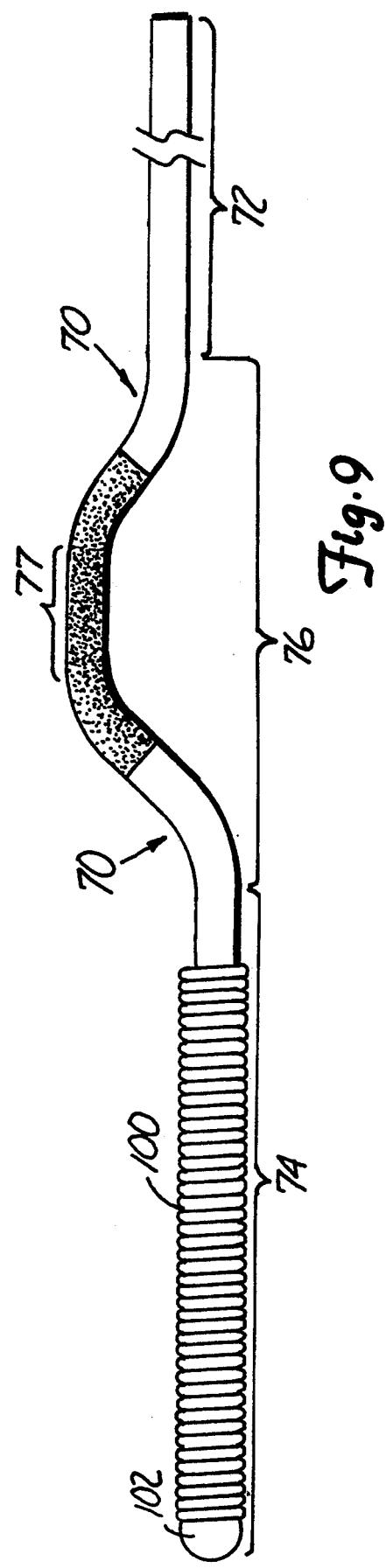

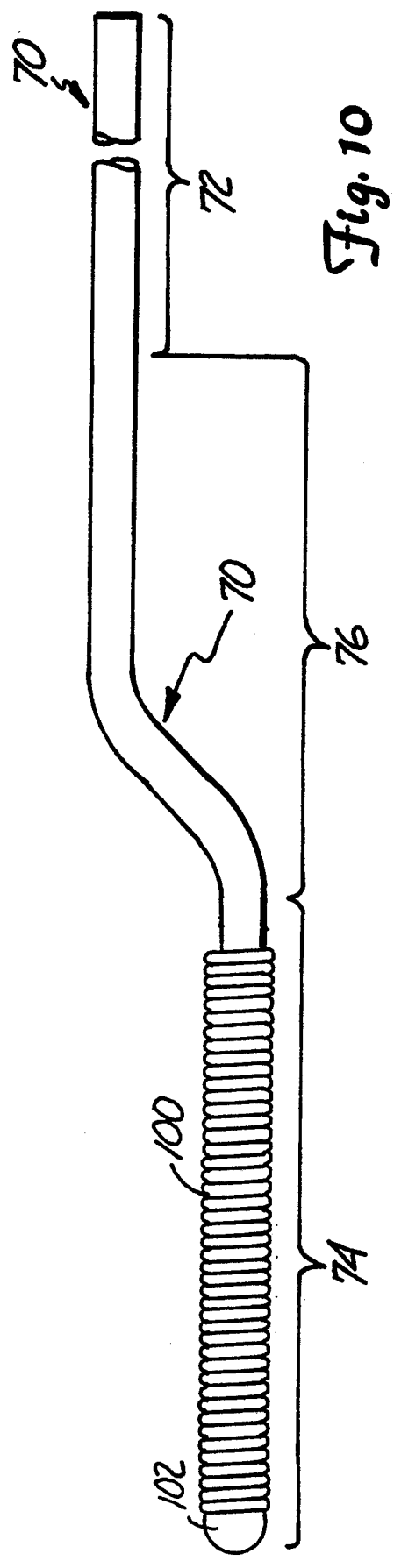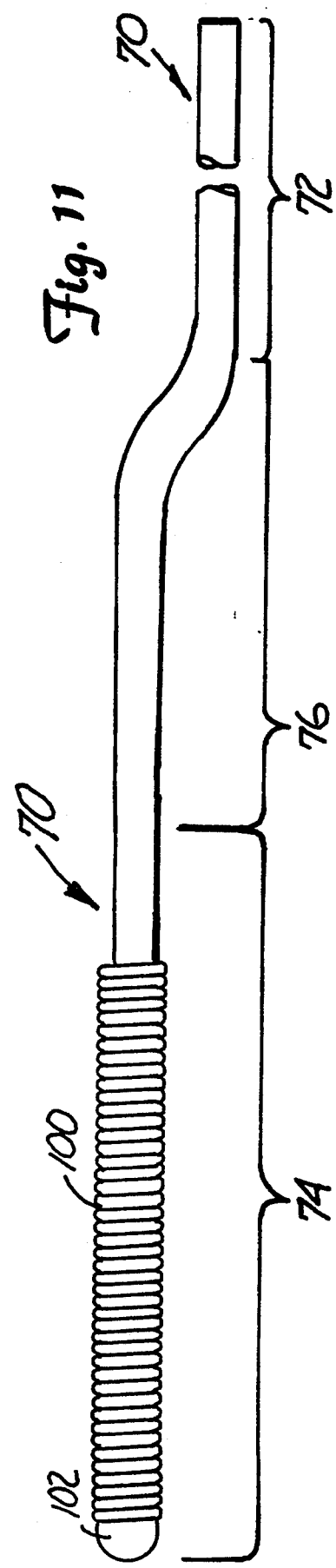

APPARATUS AND METHOD FOR ROTATIONAL ATHERECTOMY

FIELD OF THE INVENTION

The invention relates to devices and methods for removing tissue from body passageways, such as removal of atherosclerotic plaque from arteries, utilizing a rotary atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft cholesterol-rich atheromatous material hardens into a calcified atherosclerotic plaque. Such atheromas restrict the flow of blood, and therefore are often referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 5,092,873 (Simpson), a cylindrical housing, carded at the distal end of a catheter, has a portion of its side-wall cutout to form a hollow housing into which the atherosclerotic plaque can protrude when the device is positioned next to the plaque. An atherectomy blade, disposed within the housing, is then advanced the length of the housing to lance the portion of the atherosclerotic plaque that extends into the housing cavity. While such devices provide for directional control in selection of tissue to be excised, the length of the portion excised at each pass of the atherectomy blade is necessarily limited to the length of the cavity in the device—in turn, the length and relative rigidity of the housing limits the maneuverability and therefore the utility of the device in narrow and tortuous passageways such as coronary arteries.

Another approach which solves some of these problems involves the use of a rotating burr covered with an abrasive cutting material such as diamond grit (diamond particles or dust) carded at the distal end of a flexible drive shaft, similar to a dental abrading/polishing tool. Examples of such devices are illustrated in U.S. Pat. No. 4,990,134, (issued to Auth), as well as "Premier Two Striper ® Gingival Curettage" (Abrasive Technology, Inc. 1982); "Premier Two Striper ® Crown & Bridge Techniques" (Abrasive Technology, Inc. 1981); H. Gilmore, et. al, *Operative Dentistry* (C. V. Mosby Company 1982, 4th ed.), pp. 64–65, 69, 348–350; R. Tupac, et al., "A Comparison of Cord Gingival Displacement With the Gingitage Technique," *Journal of Prosthetic Dentistry*, (November 1981, pp.509–515); and Premier Presents Two Striper ® Dental Diamond Instruments (Abrasive Technology, Inc. 1989). The burr in such devices is rotated at speeds in the range of 20,000 to 200,000 rpm or more, which, depending on the diameter of the burr, can provide surface speeds of the abrasive particles on the burr above or below 40 ft/sec. Auth claims that at surface speeds below 40 ft/sec the abrasive burr will remove hardened atherosclerotic material but will not damage normal elastic soft tissue of the vessel wall. Auth also admits that at surface speeds above 40 ft/sec the abrasive burr will remove both hardened and soft tissue. See, e.g., U.S. Pat. No. 4,990,134 at col. 3, lines 20–23. Unfortunately not all atherosclerotic plaques are hardened, calcified atherosclerotic plaques. Moreover, the mechanical properties of the soft plaques are very often quite close to the mechanical properties of the soft wall of the vessel. Thus, one cannot safely rely entirely on the differential cutting properties of such abrasive burrs to remove atherosclerotic material from an arterial wall, particularly where one is attempting to entirely remove all or almost all of the atherosclerotic material. See, e.g., *Atherectomy, A Physicians Guide*, (Strategic Business Development, Inc., 1990), pp. 89, 94–96. Furthermore, the Auth burr effectively blocks blood flow through the artery during the passage of the burr through the stenosis, thus limiting the amount of time of each pass across the stenosis to less than one minute (and perhaps as little as 10 seconds). See id. at pp. 95–96. Because the size of the particles removed by the Auth burr is very small (typically 5 microns or less), and because of the time limitations described above, in clinical practice, in order to remove a sufficient amount of tissue during each pass of the burr across the stenosis, the Auth burr is virtually always rotated at speeds of at least about 155,000 rpm. At such speeds a diamond dust covered burr with a diameter of 1.5 mm achieves a surface speed of 40 ft/sec, the very speed at which the differential cutting effect becomes limited, at best (i.e., the burr removes both hard and soft tissue).

The ability of diamond dust covered burrs to remove human soft tissue at high surface speeds (e.g., small diameter burrs rotated at about 200,000 rpm) has been known for some time and has been utilized in dentistry since at least the early 1980's to remove soft gum tissue (see, e.g., "Premier Two Striper ® Gingival Curettage" (Abrasive Technology, Inc. 1982); "Premier Two Striper ® Crown & Bridge Techniques" (Abrasive Technology, Inc. 1981); H. Gilmore, et. al, *Operative Dentistry* (C. V. Mosby Company 1982, 4th ed.), pp. 348–350; R. Tupac, et al., "A Comparison of Cord Gingival Displacement With the Gingitage Technique," *Journal of Prosthetic Dentistry*, (November 1981, pp.509–515).

Several problems have been recognized in use of the Auth-type of burr, however. First, although under some conditions the differential cutting properties of such burrs are effective to protect healthy tissue, in many circumstances the burr nevertheless can abrade at least a portion of the healthy tissue, creating a risk of perforation. This is particularly true at higher rotational speeds. A majority of atherosclerotic lesions are asymmetrical (i.e., the atherosclerotic plaque is thicker on one side of the artery than on the other). Moreover, pressure of the burr against the atherosclerotic plaque is achieved only by the use of a burr having a diameter slightly larger than the opening through the stenotic passageway. Thus, since the stenotic material will be entirely removed on the thinner side of an eccentric lesion before it will be removed on the other, thicker side of the lesion, during removal of the remaining thicker portion of the atherosclerotic plaque the burr necessarily will be engaging healthy tissue on the side which has been cleared—indeed, lateral pressure by such healthy tissue against the burr is required to keep the burr in contact with the remaining stenotic tissue on the opposite wall of the passageway. For stenotic lesions that are entirely on one side of an artery (a relatively frequent condition), this means that the healthy tissue across from the stenotic lesion will be exposed to and in contact with the abrasive burr for substantially the entire procedure. Moreover, pressure from that healthy tissue against the burr will be, in fact, the only pressure urging the burr against the atherosclerotic plaque. Under these conditions, a certain amount of damage to the healthy tissue is almost unavoidable, even though undesirable, and there is a clear risk of perforation. Thus, in clinical practice (balancing safety and residual stenosis), physicians rarely use a burr diameter of more than 2 mm, even on patients where the original diameter of the coronary artery lumen is estimated to be 3 mm. See, e.g., *Atherectomy, A Physicians Guide*, (Strategic Business Development, Inc., 1990), p. 96. These risks are enhanced at high rotational speeds where the differential cutting phenomenon is significantly diminished.

As indicated above, in clinical practice the opening of the stenosis of coronary (heart) arteries using the Auth-type burr is performed very fast and thus very large numbers of small particles of stenotic material (estimated to be 1,000,000 per cubic mm of stenotic material removed—see id. at p. 92) are released into the coronary artery within a very short period of time. Although individually the particles (typically in the range of 5 microns) can easily pass through the capillaries, when such large numbers of such particles are released within a very short period of time it is very possible that there is a risk that they may at least temporarily occlude the capillaries. This may explain the heart pain which is not infrequently experienced by patients immediately after the Auth-type burr is passed across the stenosis, as well as elevated levels of enzymes indicative of myocardial ischemia (such as CPK) which have been documented in some patients after the Auth-type burr procedure. See id. at p. 95.

It would therefore be advantageous to provide an abrasive burr based instrument which can provide directional control of removal of stenotic tissue allowing one to effectively remove eccentrically located stenotic material (e.g., atherosclerotic plaque) without any risk of damage (and thus risk of perforation) to normal vascular wall not covered with stenotic material. It would also be advantageous to provide such an instrument that would not completely occlude the blood flow through an artery during the atherectomy procedure, thus, not limiting the time available to the physician to open the stenosis. Furthermore, it would be advantageous to provide such an instrument that would allow slower, controlled release of particles of stenotic material into the capillaries over a longer period of time, thus reducing or eliminating the possibility of temporary cardiac ischemia (as evidenced by CPK elevation) and heart pain associated with passage of the burr across the stenosis. Also, it would be advantageous to provide a small diameter burr-based instrument capable of opening stenoses in large diameter peripheral arteries (such as the femoral and iliac arteries) without resorting to entry through a cut-down on the femoral artery.

SUMMARY OF THE INVENTION

The invention relates to the use of a rotational atherectomy device with a guide wire that gives directional control over the position of the atherectomy device's abrasive burr within a body passageway, thereby providing a method for controlled removal of tissues from body passageways, such as atherosclerotic plaques from arteries. The rotational atherectomy device includes a rotatable abrasive burr carded at a distal end of a flexible, elongated drive shaft. The drive shaft in turn typically is disposed in a catheter having a central lumen with a longitudinal axis and a distal end, the drive shaft being operatively connected to means for rotating the drive shaft at high speeds. The guide wire comprises a flexible, generally straight proximal portion, a flexible distal tip portion, and a flexible intermediate burr-positioning segment with a predetermined curved shape. This curved intermediate burr-positioning segment of the guide wire controls the lateral position of the burr within the body passageway and is, in fact, responsible for directional control over the rotational atherectomy device. The guide wire is sized so that its proximal end can be inserted into the distal end of the drive shaft lumen, permitting the drive shaft and burr to be advanced longitudinally over the guide wire to locate the burr along the predetermined shape of such intermediate burr-positioning segment, thereby selectively positioning the burr laterally away from the longitudinal axes of the proximal and distal portions of the guide wire.

The lateral position of the burr within the body passageway is controlled by the degree of lateral deflection and the orientation of the curve of the intermediate burr-positioning segment of the guide wire. Thus, by advancing or retracting the drive shaft and burr with respect to the guide wire, the burr can be selectively located along the burr-positioning segment of the guide wire to selectively position the burr laterally of the axes of the proximal and distal portions of the guide wire. Guide wires having intermediate burr-positioning segments with different shapes can be used to control both the lateral position and the angular orientation of the burr, providing great flexibility in positioning the burr to remove unwanted tissue (such as an atherosclerotic plaque).

In a preferred embodiment, the shaft of the guide wire is made of a shape-memory alloy, such as nitinol. The fabrication of the guide wire shaft from such shape-memory alloys assures preservation of the configuration of the intermediate burr-positioning segment of the guide wire even after it is advanced around very tortuous curves in the body passageway.

The method of removing tissue from a body passageway begins by selecting a rotational atherectomy device with an appropriate abrasive burr size (diameter) and a guide wire for directional rotational atherectomy with an appropriate burr-positioning segment. The guide wire is advanced into the body passageway until its distal end extends across the stenosis. Then the burr, the flexible drive shaft, and the catheter (with the drive shaft disposed in the lumen of the catheter), are advanced over the guide wire until the burr is located longitudinally over the burr-positioning segment of the guide wire and just proximally to the stenotic tissue to be removed. The guide wire is then rotated (if necessary,) to position the burr rotationally within the passageway to a position where the physician will begin to remove tissue (typically the thickest part of the stenosis).

The flexible drive shaft and burr are rotated at relatively high speed to abrade the tissue of interest. As the burr is rotated, it is moved distally and proximally (either together with or independently of the guide wire and the catheter) in the passageway, removing a portion of the tissue of interest (e.g., atherosclerotic plaque) as it is moved. The burr-positioning segment causes the burr to be urged laterally against the stenotic tissue. The rotational position of the burr with respect to the stenotic tissue can be controlled by rotating the guide wire (and thus the positioning segment) in the body passageway.

The invention provides several distinct advantages over devices such as the Auth and Simpson atherectomy devices. With respect to Auth-type devices, there are a number of advantages to the present invention:

1. It provides directional control over the removal of stenotic tissue, reducing the risk of damage to or perforation of the normal vascular wall;
2. It provides a small diameter burr-based instrument capable of opening stenoses in large diameter peripheral arteries (such as the femoral and iliac arteries) without resorting to entry through a cut-down on the femoral artery;
3. It does not completely occlude the blood flow through an artery during an atherectomy procedure, thus not limiting the time available to the physician to open the stenosis; and
4. It provides for slower, controlled release of particles of stenotic material into the capillaries over a longer period of time.

With respect to the Simpson-type atherectomy devices, the invention provides at least two additional advantages:

1. It is very flexible (compared to Simpson-type devices which typically have a rigid housing), permitting its use in small, more tortuous arteries; and
2. It provides the ability to remove hard, calcified stenotic tissue.

BRIEF DESCRIPTION OF THE DRAWINGS

FIG. 1 is a partially broken away view of the apparatus of the invention, shown somewhat schematically and in cross-section, with a rotational atherectomy device advanced over the guide wire, and with the burr located over the intermediate burr-positioning segment of the guide wire;

FIGS. 2-7 depict a sequence of steps in use of the apparatus of the invention in removing a stenosis in an artery—FIG. 2 is a partially broken away view of the rotational atherectomy device of the apparatus of the invention inserted into an artery having a stenosis to be removed, the burr being located at the top of the burr-positioning segment of the guide wire, and just proximally to and on the side of the stenosis;

FIG. 3 is a view similar to FIG. 2 with both the guide wire and the burr advanced forward partially across the stenosis, the burr having removed a proximal portion of an inner layer of the atherosclerotic plaque;

FIG. 4 is a view similar to FIGS. 2-3 with the entire inner layer of the atherosclerotic plaque having been removed;

FIG. 5 is a view similar to FIG. 4, with the burr (and rotational atherectomy device) being withdrawn;

FIG. 6 is a view similar to FIG. 5, with the rotational atherectomy device having been reinserted with a larger burr for continued removal of the stenosis;

FIG. 7 is a view similar to FIG. 6 with both the guide wire and the larger burr advanced forward across the stenosis, the burr having removed almost all of the outer layer of the atherosclerotic plaque;

FIG. 8 illustrates a guide wire of the apparatus of the invention having a predetermined lateral deflection of the intermediate burr-positioning segment;

FIG. 9 illustrates a guide wire having a radio-opaque marker (coating) on its intermediate burr-positioning segment;

FIG. 10 is a view similar to FIG. 8, illustrating a guide wire of the invention having a different curved shape; and FIG. 11 is another view similar to FIG. 8, illustrating a guide wire of the invention having another curved shape.

BEST MODE FOR CARRYING OUT THE INVENTION

Although the drawings illustrate use of the apparatus of the invention in connection with removal of stenotic tissue in arteries, the device is usable in other capacities, wherever tissue or obstructions are desired to be removed from a body passageways, cavities, or any organ or organ system of the body.

FIG. 1 illustrates the principal components of the guide wire and rotational atherectomy device of the invention. An elongated catheter 20 includes at least one lumen 26. In this lumen 26 of the catheter 20, a multistrand helically wound flexible drive shaft 50 is disposed. The shaft 50 is generally comprised of a helical coil 52, at least the distal portion of which is preferably encased in a thin, flexible Teflon ® sheath 54. An abrasive burr 40 is carried at the distal end of the flexible drive shaft 50, the burr including a central lumen 46 generally co-axial of the central lumen 56 of the flexible drive shaft.

A guide wire 70, specially configured and arranged for selective removal of atherosclerotic tissue that is located predominantly on one side of an arterial wall (a procedure sometimes referred to as directional rotational atherectomy), is disposed in the lumen 56 of the flexible drive shaft 50. The guide wire 70 includes a flexible, generally straight, proximal portion 72, a conventional flexible distal tip portion 74, and a flexible intermediate burr positioning segment 76 which has a predetermined curved shape. The shape illustrated in FIG. 1 is such that the abrasive burr 40 is positioned laterally away from the longitudinal axes of the proximal and distal portions 72 and 74, respectively, of the guide wire 70.

The proximal portion of the catheter 20, as shown in the lower haft of FIG. 1, is secured to a housing 34. A turbine 35 (or equivalent source for rotational motion) is secured to a turbine mount 37 slidably received in the housing 34. Relative longitudinal sliding movement of the turbine mount 37 with respect to the housing 34 is permitted, and, when it is desired to lock the longitudinal position of the turbine 35 and turbine mount 37 with respect to the housing 34, wing nuts 38 can be tightened on threaded bolts 39 (which extend from the turbine mount 37 through slots 36 in the housing 34). Alternately, equivalent means may be used to prevent relative longitudinal movement of the turbine and turbine mount with respect to the housing.

The turbine 35 is connected by way of turbine link 64 to the flexible drive shaft 50. A conventional seal 66 may be provided against the outer surface of the turbine link 64, preventing fluid from escaping from the cavity 65 while permitting rotational and longitudinal movement of the flexible drive shaft 50 and the turbine linkage 64. A side port 67 may be provided to permit infusion of lubricating fluid (saline or glucose solutions and the like) or radio-opaque contrast solutions into the cavity 65 and the lumen 26 of the catheter 20. The side port 67 could also be connected to a vacuum source for aspiration of fluid through the catheter's lumen 26.

Set screws 61 and 62 are provided to selectively permit or prevent relative longitudinal movement of the guide wire 70 with respect to the turbine mount 37 and with respect to the housing 34. Thus, if the set screw 62 is loosened while the screw 61 is tightened against the guide wire, the guide wire 70 and the flexible drive shaft 50 (which is rigidly connected to the turbine 35 and hence to the turbine mount 37) can be advanced and retracted as a unit with respect to the catheter 20 and the housing 34. Alternately, loosening of set screw 61 and tightening of set screw 62 will permit relative longitudinal movement of the flexible drive shaft and the burr with respect to the guide wire 70 allowing one to locate the burr at an appropriate place on the burr-positioning segment 76 of the guide wire 70. When both set screws 61 and 62 are loosened then obviously one can move the guide wire 70 longitudinally with respect to both the catheter 20 and the flexible drive shaft (and, hence, the burr).

A guide wire handle 78 can be secured to the proximal end portion of the guide wire 70 by set screw 79 to facilitate rotation of the guide wire 70 with respect to the catheter 20 (and thus the patient's artery, so long as the catheter 20 and housing 34 are not rotated). Set screws 61 and 62 must be loosened to permit such rotational movement; tightening either of such set screws will secure the guide wire rotationally with respect to the housing 34 and catheter 20.

Although the means for securing the guide wire 70, the turbine mount 37, and the housing 34 with respect to one another are illustrated in the drawing as being accomplished by use of wing nuts 38 and set screws 61 and 629 it will be appreciated that other conventional means or mechanisms (such as cam friction fittings, and the like) may easily be employed. Similarly, the guide wire handle 78 can be secured to the guide wire using such cam friction type or equivalent mechanisms. Moreover, the connection of the proximal end of the catheter 20 to the housing 34, as well as the side port 67, are shown somewhat schematically—any of a variety of conventional fittings that are readily commercially available or adaptable for this purpose may easily be employed.

FIGS. 2–7 illustrate the operation and function of the invention for removing an atherosclerotic lesion or atheroma 12 from an artery 10. As indicated above, the guide wire of the invention is particularly useful in removing asymmetrical stenotic lesions, such as the one illustrated in FIGS. 2–7. Although the guide wire will work just as well with symmetrical stenotic lesions or only mildly asymmetrical stenotic lesions, the advantages of the invention are best illustrated with respect to an atherosclerotic lesion that is located predominantly on one side of the arterial wall 10.

Commercially available angioplasty equipment (e.g., arterial puncture needles, arterial dilators, sheath introducers and guide catheters) and routine angioplasty techniques are used to appropriately position the guide wire of the invention in the arteries of interest.

In FIG. 2, the guide wire 70 has been advanced into the artery 10 until its distal end 74 extends across the stenosis 12. At this point, the burr 40, flexible drive shaft 50, and the catheter 20 (with the drive shaft 50 disposed in the lumen 26 of the catheter 20), are advanced over the guide wire 70 until the burr 40 is located longitudinally over the burr-positioning segment 76 of the guide wire 70 and just proximally to the stenotic tissue 12 to be removed. The guide wire 70 is then rotated (if necessary) using the guide wire handle 78 to position the burr 40 rotationally within the artery 10 to a position where the physician will begin to remove the stenotic tissue 12 (typically at the thickest part of the stenosis).

The flexible drive shaft 50 and burr 40 are rotated at relatively high speed (typically in the range of about 30,000 RPM to about 600,000 RPM, or even more, depending only on the physical dimension and capabilities of the turbine/motor, guide wire, flexible drive shaft and burr) to selectively remove an inner layer of the stenotic lesion 12. As the burr 40 is rotated, it is moved distally and proximally (either together with or independent of the guide wire 70 and the catheter 20) in the artery 10, removing a portion of the atherosclerotic plaque 12 as it is moved. The burr-positioning segment 76 causes the burr 40 to be urged laterally against the stenotic tissue 12. The rotational position of the burr 40 with respect to the stenotic tissue 12 can be controlled by rotating the guide wire 70 (and thus the positioning segment 76) in the artery 10 using the guide wire handle 78.

In FIG. 3, the burr 40, together with the guide wire 70 and the catheter 20, has been advanced forward partially across the stenosis 12, having removed a proximal portion of the inner layer of the atherosclerotic plaque 12.

In FIG. 4, all of the inner layer of the stenotic lesion 12 within reach of the burr 40 and the burr-positioning segment of the guide wire 70 has been removed. The removal of all of the inner layer of the atherosclerotic plaque 12 from the circumference of the artery may require rotation of the guide wire to several rotational positions, followed by successive distal and proximal movement of the burr 40 and guide wire 70 at each such rotational position. After all of this inner layer of the stenotic lesion has been removed, there is no significant further pressure of the burr 40 against the atherosclerotic lesion 12. Consequently, as illustrated in FIGS. 5–6, the rotational atherectomy device, with the burr 40, can then be removed from the guide wire 70 and replaced with a different rotational atherectomy device having a larger diameter burr 40, allowing one to remove the outer layer of atherosclerotic plaque 12. More of the atherosclerotic lesion 12 can then be removed, as illustrated in FIG. 7. When a sufficient amount of the lesion 12 has been removed, the entire device, including the guide wire, can be withdrawn.

As can be seen from the above discussion in reference to the drawings, during the entire procedure the abrasive burr 40 never need come into contact with the wall 10 of the artery across from the atherosclerotic lesion 12. Rather, the invention provides directional control over the lateral location of the burr within the artery, permitting contact of the burr substantially only with stenotic tissue 12. Concerns about damage to healthy tissue (including concerns about perforation) are thus substantially reduced.

Moreover, lumens of very large arteries can be reopened to their original diameter (e.g., 5–7 mm in the iliac and femoral arteries) with use of a comparatively small abrasive burr (e.g., 2 mm in diameter), a capability not practically possible with the Auth-type device, which usually requires performing a cut-down on the common femoral artery in order to introduce the larger burrs (e.g., over 3 or 4 mm in diameter) of the Auth-type device.

Conventional fluoroscopic imaging techniques (with or without radio-opaque contrast solution injections) should be utilized in performing the directional rotational atherectomy procedure. The longitudinal and rotational positioning of the guide wire 70 and the burr 40 within the artery 10 may be assisted by placing special radio-opaque markings on the guide wire 70. For this purpose, as illustrated in FIG. 9, a conventional radio-opaque marking can be placed on the burr-positioning segment 76 of the guide wire 70. Such markings may simply comprise a thin layer of gold, platinum or similar radio-opaque material.

The burr-positioning segment 76 of the guide wire 70 can be configured into a variety of suitable shapes with varying maximal heights of its curve to provide control over the degree of lateral deflection of the burr 40 when it is positioned over the burr-positioning segment. FIG. 8 illustrates a typical configuration. Preferably the burr-positioning segment is generally co-planar; i.e., the curves of this segment are all made is the same plane so that, as viewed in the drawings, the wire would lie flat. The curves of the burr-positioning segment preferably are formed so that the longitudinal axis 97 of the central portion 77 of the burr-positioning segment 76 is spaced a distance $H_1$ laterally to one side of the longitudinal axis 92 of the proximal portion 72 of the guide wire 70. It is this lateral displacement of the burr-positioning segment 76 that provides control over the degree of lateral displacement of the burr 40 within the artery. Accordingly, rotation of the guide wire (when the burr is located over the burr-positioning segment) provides directional control over the rotational position of the burr 40 within the artery. The distance $H_1$ is selected based on the relative size of the artery and the degree of stenosis, as well as the size of the burr selected to be used. Guide wires having smaller $H_1$ distances are useful in smaller arteries and arteries with tighter stenoses. Conversely, guide wires with larger $H_1$ distances are useful in larger passageways and those with lesser degrees of stenosis.

Although the preferred amount of deflection provided by the burr-positioning segment 76 will vary from one application to another, preferably the curved burr-positioning segment 76 is shaped so that when the burr 40 is positioned at the point of greatest deflection of such segment 76, the axis of the burr 40 is positioned away from one or both of the longitudinal axes 92 and 94 of the proximal and the distal end portions of the guide wire 70 by a distance not less than about one half the diameter of the guide wire 70, and, more preferably, not less than about the diameter of the guide wire 70 (measured at the burr-positioning segment 76 of the guide wire 70). The range of deflection most preferred in coronary arteries typically will be from about 0.5 mm to about 3.5 mm. In larger peripheral arteries (such as the iliac or femoral arteries), the maximum amount of deflection can be up to about 8 mm.

In the preferred embodiment shown in FIG. 8, the longitudinal axis 92 of the proximal portion 72 of the guide wire 70 is not coaxial with the longitudinal axis 94 of the distal portion 74 of the guide wire. As can be seen by reference to FIG. 3, during the procedure the outer surface of the catheter 20 lies against the inner wall of the artery 10, as does the distal portion 74 of the guide wire 70. Preferably the guide wire is formed so that the longitudinal axis 94 of the distal portion 74 of the guide wire is offset from the longitudinal axis 92 of the proximal portion 72 by a distance $H_2$, which is equal to the distance, measured near the distal end of the catheter 20, from the outer surface of the guide wire's proximal portion 72 to the outer surface of the catheter 20, thus accounting for the fact that the proximal portion of the guide wire 70 is contained within the drive shaft and catheter, while the distal portion of the guide wire abuts directly the artery wall.

FIG. 10 illustrates an alternate embodiment where the proximal portion 72 of the guide wire 70 is generally coaxial with the proximal portion of the burr-positioning segment 76. FIG. 11 shows yet another embodiment where the distal end portion 74 is generally coaxial with the distal portion of the burr-positioning segment 76. Other guide wire configurations also may be utilized, the characteristic feature of any such configuration being that it provides lateral displacement of the abrasive burr when the burr is located over the burr-positioning segment of such guide wire.

The shaft of the guide wire preferably is made of a shape-memory alloy, such as nitinol. The fabrication of the guide wire shaft from such a shape-memory alloy assures preservation of the configuration of the intermediate burr-positioning segment 76 of the guide wire 70 even after it is advanced around very tortuous curves in the body passageway.

The distal portion 74 of the guide wire 70 includes a conventional relatively flexible, helical coil 100 having a proximal end which is secured to the guide wire shaft near the shaft's distal end. A rounded tip 102 is attached to the distal end of the helical coil 100. The distal end portion 101 of the guide wire shaft, disposed within the helical coil 100, may be tapered to provide greater flexibility to the distal tip portion of the guide wire. The distal end of the guide wire shaft may be attached directly to the rounded tip 102. Alternately, as shown in FIG. 8, the distal end of the guide wire shaft may terminate short of the rounded tip 102 and be connected to the tip 102 by a safety wire 103. Such helical coil flexible distal guide wire tips are well known, such as those shown in U.S. Pat. Nos. 4,554,929 (Re. 33,911); 4,984,581; 4,799,496; and 5,069,217. The coil preferably is made of a radio-opaque material such as titanium or platinum, or alloys of these metals. The coil also may be made of stainless steel covered with coatings of radio-opaque material such as titanium, tungsten, platinum, or alloys thereof. The coil may be attached to the guide wire shaft and the rounded tip by conventional means, such as welding, soldering, brazing or suitable adhesives (typically epoxies or cyanoacrylates).

The guide wire 70 can be provided with a slippery surface coating such as TEFLON ®, silicone, a combination of silicone over TEFLON ®, or similar slippery material. A particularly slippery surface can be obtained by utilizing PHOTOLINK ™ brand surface modification commercially available from Bio-Metric Systems, Inc. of Eden Prairie, Minn.

Preferably the shape of the burr 40 is generally ellipsoidal or frusto-spherical (i.e., the abrading portion of the burr is generally spherical). Other shapes can also be used. The body of the burr can be made from various materials including metals, ceramics and the like. Preferably it is made from stainless steel and is coated with a suitable abrasive material, such as diamond powder, fused silica, titanium nitride, tungsten carbide, aluminum oxide, boron carbide, or other ceramic materials. Although the abrasive coating on the burr of the invention may utilize any of the abrasive materials mentioned above, preferably it is comprised of diamond chips (or diamond dust particles) attached to the surface of a suitable substrate, using well known techniques, such as conventional electroplating or fusion technologies (see, e.g., U.S. Pat. No. 4,018,576). Burrs of this type have been used in a variety of medical/dental applications for years and are commercially available from companies such as Abrasive Technologies, Inc. of Westerville, Ohio.

The burr 40 can be attached to the drive shaft 50 by any suitable means, including brazing, adhesives, and the like. Suitable adhesives include epoxy resins, cyanoacrylates, and the like.

The catheter 20 can be made from conventional catheter materials, including flexible thermoplastic or silicone materials. For example, the catheter preferably is made from a slippery material such as TEFLON ®, and can be reinforced with an outer layer made of nylon or other similar materials having desirable torque transmitting characteristics.

While a preferred embodiment of the present invention has been described, it should be understood that various changes, adaptations and modifications may be made therein without departing from the spirit of the invention and the scope of the appended claims.

What is claimed is:

1. Apparatus for performing an atherectomy, comprising:
   a rotational atherectomy device having a flexible, elongated drive shaft and an abrasive burr carried on the drive shaft, the drive shaft and abrasive burr each including a central lumen therein for receipt of a guide wire; and
   a guide wire having a flexible, generally straight proximal portion, a flexible distal end portion, each such portion having a longitudinal axis, the longitudinal axis of at least a portion of the flexible distal end portion being normally substantially parallel to the longitudinal axis of the proximal portion, and flexible intermediate burr-positioning segment means having a predetermined curved shape for laterally positioning the abrasive burr with respect to one or both of the proximal portion and the distal end portion of the guide wire so that when the abrasive burr is advanced over the guide wire to a position along the curved burr-positioning segment means, such curved burr-positioning segment means positions the burr laterally away from one or both of such longitudinal axes.

2. The apparatus of claim 1 wherein the intermediate flexible burr-positioning segment has a predetermined curved shape such that it positions the burr laterally away from the longitudinal axis of the proximal portion of the guide wire.

3. The apparatus of claim 1 wherein the intermediate flexible burr-positioning segment has a predetermined curved shape such that it positions the burr laterally away from the longitudinal axis of the distal end portion of the guide wire.

4. The apparatus of claim 1 wherein the intermediate flexible burr-positioning segment has a predetermined curved shape such that it positions the burr laterally away from the longitudinal axes of both the distal end portion and the proximal portion of the guide wire.

5. The apparatus of claim 1 wherein the rotational atherectomy device includes a catheter in which the drive shaft is disposed, the catheter and the guide wire each having an outer surface, the curve of the guide wire's burr-positioning segment being configured so that the axes of the portions of the guide wire which are located just proximal and distal to the intermediate burr-positioning segment are offset from each other by an amount generally equal to the cross-sectional distance, measured at the distal end of the catheter, between the outer surface of the guide wire and the outer surface of the catheter.

6. The apparatus of claim 1 wherein the guide wire is made substantially of a shape-memory alloy.

7. The apparatus of claim 6 wherein the shape-memory alloy is nitinol.

8. The apparatus of claim 1 wherein the burr-positioning segment is generally co-planar throughout its curved shape.

9. The apparatus of claim 1 wherein the burr includes a central, longitudinal axis, the curved burr-positioning segment being shaped so that when the burr is positioned at the point of greatest deflection of such segment, the axis of the burr is positioned away from one or both of the longitudinal axes of the proximal and the distal end portions of the guide wire, by a distance not less than about the diameter of the guide wire, measured at the burr-positioning segment of the guide wire.

10. Apparatus for performing an atherectomy, comprising:
    a rotational atherectomy device having a flexible, elongated drive shaft, an abrasive burr carried on the drive shaft, the drive shaft and abrasive burr each including a central lumen therein for receipt of a guide wire, and a catheter in which the drive shaft is disposed, the catheter and the guide wire each having an outer surface; and
    a guide wire having a flexible, generally straight proximal portion, a flexible distal end portion, each such portion having a longitudinal axis, and a flexible intermediate burr-positioning segment, the burr-positioning segment being made of a shape-memory alloy and having a predetermined curved shape, which is generally co-planar, such that when the abrasive burr is advanced over the guide wire to a position along the curved burr-positioning segment, such curved segment positions the burr laterally away from the longitudinal axes of the proximal and distal end portions;
    the curve of the guide wire's burr-positioning segment being configured so that the axes of the portions of the guide wire which are located just proximal and distal to the intermediate burr-positioning segment are offset from each other by an amount generally equal to the cross-sectional distance, measured at the distal end of the catheter, between the outer surface of the guide wire and the outer surface of the catheter.

11. Apparatus for performing an atherectomy, comprising:
    a rotational atherectomy device having a flexible, elongated drive shaft, an abrasive burr carried on the drive shaft, the drive shaft and abrasive burr each including a central lumen therein for receipt of a guide wire, and a catheter in which the drive shaft is disposed, the catheter and the guide wire each having an outer surface; and
    a guide wire having a flexible, generally straight proximal portion, a flexible distal end portion, each such portion having a longitudinal axis, and a flexible intermediate burr-positioning segment, the burr-positioning segment being made of a shape-memory alloy and having a predetermined curved shape, which is generally co-planar, the curved shape being configured so that the axes of the portions of the guide wire which are located just proximal and distal to the intermediate burr-positioning segment are offset from each other such that when the abrasive burr is advanced over the guide wire to a position along the burr-positioning segment, such segment positions the burr laterally away from the longitudinal axis of the distal end portion of the guide wire.

12. Apparatus for performing an atherectomy, comprising:
- a rotational atherectomy device having a flexible, elongated drive shaft, an abrasive burr carried on the drive shaft, the drive shaft and abrasive burr each including a central lumen therein for receipt of a guide wire, and a catheter in which the drive shaft is disposed, the catheter and the guide wire each having an outer surface; and
- a guide wire having a flexible, generally straight proximal portion, a flexible distal end portion, each such portion having a longitudinal axis, and a flexible intermediate burr-positioning segment, the burr-positioning segment being made of a shape-memory alloy and having a predetermined curved shape, which is generally co-planar, the curved shape being configured so that the axes of the portions of the guide wire which are located just proximal and distal to the intermediate burr-positioning segment are offset from each other such that when the abrasive burr is advanced over the guide wire to a position along the burr-positioning segment, such segment positions the burr laterally away from the longitudinal axis of the proximal portion of the guide wire.

13. A method of removing a stenosis from an artery comprising the steps of:
(a) providing a rotational atherectomy device having a flexible, elongated drive shaft with an abrasive burr carried on the drive shaft, the drive shaft and abrasive burr each including a central lumen therein for receipt of a guide wire;
(b) providing a guide wire having a flexible, generally straight proximal portion, a flexible distal end portion, each such portion having a longitudinal axis, and a flexible intermediate burr-positioning segment having a predetermined curved shape;
(c) advancing the guide wire across the stenosis in the artery and positioning the burr-positioning segment of the guide wire near stenotic tissue to be removed;
(d) advancing the burr with its flexible drive shaft along the guide wire to a position along the burr-positioning segment, generally just proximal to the stenotic tissue to be removed, such burr-positioning segment thereby positioning the burr laterally away from one or both of the longitudinal axes of the proximal and the distal end portions of the guide wire;
(e) rotating the guide wire, if necessary, to position the burr at a desired location adjacent to the tissue to be removed; and
(f) rotating the drive shaft and burr while advancing and retracting the burr and drive shaft to remove the tissue.

14. The method of claim 13 further wherein the advancing and retracting step includes the steps of advancing or retracting the burr across a portion of the tissue to be removed, rotating the guide wire to position the burr at a new desired location with respect to the tissue to be removed, and again advancing or retracting the burr across such tissue to remove more of the tissue.

* * * * *